United States Patent
MacDonald et al.

(10) Patent No.: US 7,879,350 B2
(45) Date of Patent: Feb. 1, 2011

(54) METHOD FOR REDUCING ODOR USING COLLOIDAL NANOPARTICLES

(75) Inventors: John Gavin MacDonald, Decatur, GA (US); Kevin P. McGrath, Alpharetta, GA (US); Irene Kuznetsov, Lawrenceville, GA (US); Jaeho Kim, Roswell, GA (US); Lei Huang, Duluth, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 2031 days.

(21) Appl. No.: 10/686,933

(22) Filed: Oct. 16, 2003

(65) Prior Publication Data

US 2005/0084412 A1 Apr. 21, 2005

(51) Int. Cl.
*A61F 13/00* (2006.01)
*A61L 9/00* (2006.01)
(52) U.S. Cl. .................... 424/443; 424/76.1
(58) Field of Classification Search .............. None
See application file for complete search history.

(56) References Cited

U.S. PATENT DOCUMENTS

| | | |
|---|---|---|
| 2,015,864 A | 10/1935 | Müller et al. |
| 2,593,146 A | 4/1952 | Howard |
| 3,266,973 A | 8/1966 | Crowley |
| 3,338,992 A | 8/1967 | Kinney |
| 3,341,394 A | 9/1967 | Kinney |
| 3,381,688 A | 5/1968 | Satas |
| 3,494,821 A | 2/1970 | Evans |
| 3,502,538 A | 3/1970 | Petersen |
| 3,502,763 A | 3/1970 | Hartmann |
| 3,507,269 A | 4/1970 | Berry |
| 3,542,615 A | 11/1970 | Dobo et al. |
| 3,615,478 A | 10/1971 | Hoshino et al. |
| 3,692,618 A | 9/1972 | Dorschner et al. |
| 3,794,497 A | 2/1974 | Pratt et al. |
| 3,802,817 A | 4/1974 | Matsuki et al. |
| 3,836,633 A | 9/1974 | Beschke |
| 3,849,241 A | 11/1974 | Butin et al. |
| 3,919,437 A | 11/1975 | Brown et al. |
| 3,960,494 A | 6/1976 | Verma et al. |
| 3,971,665 A | 7/1976 | Suzuki et al. |
| 4,006,030 A | 2/1977 | Yoshida et al. |
| 4,041,203 A | 8/1977 | Brock et al. |
| 4,078,029 A | 3/1978 | Yoshida et al. |
| 4,100,324 A | 7/1978 | Anderson et al. |
| 4,101,638 A | 7/1978 | Inoue et al. |
| 4,144,370 A | 3/1979 | Boulton |
| 4,172,781 A | 10/1979 | Walk et al. |
| 4,297,233 A | 10/1981 | Gualandi |
| RE30,797 E | 11/1981 | Davis |
| RE30,803 E | 11/1981 | Davis |
| 4,313,820 A | 2/1982 | Farha, Jr. et al. |
| 4,340,563 A | 7/1982 | Appel et al. |
| 4,375,448 A | 3/1983 | Appel et al. |
| 4,407,960 A | 10/1983 | Tratnyek |
| 4,451,388 A | 5/1984 | Payne |
| 4,467,012 A | 8/1984 | Pedersen et al. |
| 4,469,746 A | 9/1984 | Weisman et al. |
| 4,488,969 A | 12/1984 | Hou |
| 4,494,278 A | 1/1985 | Kroyer et al. |
| 4,494,629 A | 1/1985 | Raeburn |
| 4,517,308 A | 5/1985 | Ehlenz et al. |
| 4,522,203 A | 6/1985 | Mays |
| 4,525,410 A | 6/1985 | Hagiwara et al. |
| 4,575,556 A | 3/1986 | Byrne et al. |
| 4,604,313 A | 8/1986 | McFarland et al. |
| 4,640,810 A | 2/1987 | Laursen et al. |
| 4,643,801 A | 2/1987 | Johnson |
| 4,655,757 A | 4/1987 | McFarland et al. |
| 4,701,218 A | 10/1987 | Barker et al. |
| 4,715,983 A | 12/1987 | Ota et al. |
| 4,725,415 A | 2/1988 | Kidd |
| 4,734,324 A | 3/1988 | Hill |
| RE32,649 E | 4/1988 | Brandt et al. |
| 4,775,585 A | 10/1988 | Hagiwara |
| 4,780,448 A | 10/1988 | Broecker et al. |
| 4,781,858 A | 11/1988 | Mizukami et al. |
| 4,783,220 A | 11/1988 | Gamble et al. |
| 4,798,603 A | 1/1989 | Meyer et al. |

(Continued)

FOREIGN PATENT DOCUMENTS

EP 0103214 B1 3/1984

(Continued)

OTHER PUBLICATIONS

Abstract of Japanese Patent No. JP04255767, Sep. 10, 1992.

(Continued)

*Primary Examiner*—Michael G Hartley
(74) *Attorney, Agent, or Firm*—Dority & Manning, P.A.

(57) ABSTRACT

A method for reducing odors is provided. In one embodiment, the method comprises contacting a substrate containing a thin coating of colloidal nanoparticles with an odorous compound. The colloidal nanoparticles have an average size of less than about 500 nanometers, a surface area of from about 50 to about 1000 square meters per gram, and a pore volume of less than about 0.5 milliliters per gram. The colloidal nanoparticles may adsorb at least about 25% of the odorous compound when contacted therewith.

19 Claims, No Drawings

U.S. PATENT DOCUMENTS

| | | |
|---|---|---|
| 4,802,473 A | 2/1989 | Hubbard et al. |
| 4,818,464 A | 4/1989 | Lau |
| 4,823,404 A | 4/1989 | Morell et al. |
| 4,823,803 A | 4/1989 | Nakamura |
| 4,904,304 A | 2/1990 | Watanabe et al. |
| 4,969,457 A | 11/1990 | Hubbard et al. |
| 4,978,615 A | 12/1990 | Aoyama et al. |
| 4,988,505 A | 1/1991 | Watanabe et al. |
| 5,000,746 A | 3/1991 | Meiss |
| 5,020,533 A | 6/1991 | Hubbard et al. |
| 5,057,302 A | 10/1991 | Johnson et al. |
| 5,064,473 A | 11/1991 | Kubo et al. |
| 5,064,599 A | 11/1991 | Ando et al. |
| 5,100,581 A | 3/1992 | Watanabe et al. |
| 5,100,702 A | 3/1992 | Maeda et al. |
| 5,102,592 A | 4/1992 | McCauley et al. |
| 5,108,739 A | 4/1992 | Kurihara et al. |
| 5,120,693 A | 6/1992 | Connolly et al. |
| 5,122,418 A | 6/1992 | Nakane et al. |
| 5,133,803 A | 7/1992 | Moffatt |
| 5,145,518 A | 9/1992 | Winnik et al. |
| 5,145,727 A | 9/1992 | Potts et al. |
| 5,169,706 A | 12/1992 | Collier, IV et al. |
| 5,178,931 A | 1/1993 | Perkins et al. |
| 5,183,656 A | 2/1993 | Uesaka et al. |
| 5,188,885 A | 2/1993 | Timmons et al. |
| 5,196,177 A | 3/1993 | Watanabe et al. |
| 5,204,111 A | 4/1993 | Handjani et al. |
| 5,204,429 A | 4/1993 | Kaminsky et al. |
| 5,209,998 A | 5/1993 | Kavassalis et al. |
| 5,220,000 A | 6/1993 | Theodoropulos |
| 5,221,497 A | 6/1993 | Watanabe et al. |
| 5,225,374 A | 7/1993 | Fare et al. |
| 5,230,953 A | 7/1993 | Tsugeno et al. |
| 5,238,518 A | 8/1993 | Okubi et al. |
| 5,245,117 A | 9/1993 | Withers et al. |
| 5,266,289 A | 11/1993 | Tsugeno et al. |
| 5,284,703 A | 2/1994 | Everhart et al. |
| 5,292,868 A | 3/1994 | Subramanian |
| 5,294,717 A | 3/1994 | Theodoropulos |
| 5,300,365 A | 4/1994 | Ogale |
| 5,314,855 A | 5/1994 | Thorpe et al. |
| 5,322,061 A | 6/1994 | Brunson |
| 5,332,432 A | 7/1994 | Okubi et al. |
| 5,338,713 A | 8/1994 | Takagi et al. |
| 5,342,876 A | 8/1994 | Abe et al. |
| 5,350,624 A | 9/1994 | Georger et al. |
| 5,366,947 A | 11/1994 | Müller et al. |
| 5,382,400 A | 1/1995 | Pike et al. |
| 5,383,450 A | 1/1995 | Hubbard et al. |
| 5,397,667 A | 3/1995 | Law et al. |
| 5,407,442 A | 4/1995 | Karapasha |
| 5,407,600 A | 4/1995 | Ando et al. |
| 5,420,090 A | 5/1995 | Spencer et al. |
| 5,427,844 A | 6/1995 | Murai et al. |
| 5,429,628 A | 7/1995 | Trinh et al. |
| 5,432,000 A | 7/1995 | Young, Sr. et al. |
| 5,451,450 A | 9/1995 | Erderly et al. |
| 5,458,864 A | 10/1995 | Tsugeno et al. |
| 5,472,775 A | 12/1995 | Obijeski et al. |
| 5,480,636 A | 1/1996 | Maruo et al. |
| 5,486,356 A | 1/1996 | Yim |
| 5,487,938 A | 1/1996 | Spencer et al. |
| 5,488,126 A | 1/1996 | Subramanian et al. |
| 5,527,171 A | 6/1996 | Soerensen |
| 5,538,548 A | 7/1996 | Yamazaki |
| 5,539,124 A | 7/1996 | Etherton et al. |
| 5,540,916 A | 7/1996 | Parks |
| 5,547,607 A | 8/1996 | Ando et al. |
| 5,553,608 A | 9/1996 | Reese et al. |
| 5,554,775 A | 9/1996 | Krishnamurti et al. |
| 5,580,655 A | 12/1996 | El-Shall et al. |
| 5,583,219 A | 12/1996 | Subramanian et al. |
| 5,591,797 A | 1/1997 | Barthel et al. |
| 5,597,512 A | 1/1997 | Watanabe et al. |
| 5,616,315 A | 4/1997 | Masterman et al. |
| 5,661,198 A | 8/1997 | Inatani et al. |
| 5,663,224 A | 9/1997 | Emmons et al. |
| 5,679,138 A | 10/1997 | Bishop et al. |
| 5,679,724 A | 10/1997 | Sacripante et al. |
| 5,695,868 A | 12/1997 | McCormack |
| 5,733,272 A | 3/1998 | Brunner et al. |
| 5,747,003 A | 5/1998 | Mohnot et al. |
| 5,762,643 A * | 6/1998 | Ray et al. ................... 604/383 |
| 5,773,227 A | 6/1998 | Kuhn et al. |
| 5,795,985 A | 8/1998 | Hüsler et al. |
| 5,813,398 A | 9/1998 | Baird et al. |
| 5,817,300 A | 10/1998 | Cook et al. |
| 5,837,352 A | 11/1998 | English et al. |
| 5,843,509 A | 12/1998 | Calvo Salve et al. |
| 5,855,788 A | 1/1999 | Everhart et al. |
| 5,858,503 A | 1/1999 | Everhart et al. |
| 5,861,144 A | 1/1999 | Peterson et al. |
| 5,871,872 A | 2/1999 | Matijevic et al. |
| 5,874,067 A | 2/1999 | Lucas et al. |
| 5,880,176 A | 3/1999 | Kamoto et al. |
| 5,880,309 A | 3/1999 | Suzuki et al. |
| 5,882,638 A | 3/1999 | Dodd et al. |
| 5,885,599 A | 3/1999 | Peterson et al. |
| 5,897,541 A | 4/1999 | Uitenbroek et al. |
| 5,902,226 A | 5/1999 | Tasaki et al. |
| 5,905,101 A | 5/1999 | Fujiki et al. |
| 5,916,596 A | 6/1999 | Desai et al. |
| 5,948,398 A | 9/1999 | Hanamoto et al. |
| 5,948,483 A | 9/1999 | Kim et al. |
| 5,962,566 A | 10/1999 | Grandfils et al. |
| 5,964,926 A | 10/1999 | Cohen |
| 5,972,389 A | 10/1999 | Shell et al. |
| 5,985,229 A | 11/1999 | Yamada et al. |
| 5,989,510 A | 11/1999 | Abe et al. |
| 5,989,515 A | 11/1999 | Watanabe et al. |
| 5,998,222 A | 12/1999 | Weimer |
| 6,004,625 A | 12/1999 | Oshima |
| 6,007,592 A | 12/1999 | Kasai et al. |
| 6,024,786 A | 2/2000 | Gore |
| 6,045,900 A | 4/2000 | Haffner et al. |
| 6,047,413 A | 4/2000 | Welchel et al. |
| 6,060,410 A | 5/2000 | Gillberg-LaForce et al. |
| 6,073,771 A | 6/2000 | Pressley et al. |
| 6,075,179 A | 6/2000 | McCormack et al. |
| 6,096,299 A | 8/2000 | Guarracino et al. |
| 6,111,163 A | 8/2000 | McCormack et al. |
| 6,172,173 B1 | 1/2001 | Spencer et al. |
| 6,177,608 B1 | 1/2001 | Weinstrauch |
| 6,190,814 B1 | 2/2001 | Law et al. |
| 6,193,844 B1 | 2/2001 | McLaughlin et al. |
| 6,200,555 B1 | 3/2001 | Nishijima et al. |
| 6,210,625 B1 | 4/2001 | Matsushita et al. |
| 6,225,524 B1 | 5/2001 | Guarracino et al. |
| 6,238,767 B1 | 5/2001 | McCormack et al. |
| 6,254,894 B1 | 7/2001 | Denkewicz, Jr. et al. |
| 6,264,615 B1 | 7/2001 | Diamond et al. |
| 6,277,346 B1 | 8/2001 | Murasawa et al. |
| 6,277,489 B1 | 8/2001 | Abbott et al. |
| 6,277,772 B1 | 8/2001 | Gancet et al. |
| 6,291,535 B1 | 9/2001 | Watanabe et al. |
| 6,294,222 B1 | 9/2001 | Cohen et al. |
| 6,299,867 B1 | 10/2001 | Aoyagi et al. |
| 6,309,736 B1 | 10/2001 | McCormack et al. |
| 6,315,864 B2 | 11/2001 | Anderson et al. |
| 6,334,988 B1 | 1/2002 | Gallis et al. |
| 6,344,218 B1 | 2/2002 | Dodd et al. |
| 6,344,272 B1 | 2/2002 | Oldenburg et al. |
| 6,358,537 B1 | 3/2002 | Hoshino et al. |

| | | |
|---|---|---|
| 6,358,909 B1 | 3/2002 | Ochomogo et al. |
| 6,361,780 B1 | 3/2002 | Ley et al. |
| 6,361,944 B1 * | 3/2002 | Mirkin et al. .................. 435/6 |
| 6,369,290 B1 | 4/2002 | Glaug et al. |
| 6,376,741 B1 | 4/2002 | Guarracino et al. |
| 6,387,495 B1 | 5/2002 | Reeves et al. |
| 6,398,827 B1 | 6/2002 | Ota et al. |
| 6,410,616 B1 | 6/2002 | Harada et al. |
| 6,410,765 B1 | 6/2002 | Wellinghoff et al. |
| 6,425,530 B1 | 7/2002 | Coakley |
| 6,427,693 B1 | 8/2002 | Blackstock et al. |
| 6,428,814 B1 | 8/2002 | Bosch et al. |
| 6,432,872 B1 | 8/2002 | Tsushio et al. |
| 6,433,243 B1 | 8/2002 | Woltman et al. |
| 6,440,187 B1 | 8/2002 | Kasai et al. |
| 6,460,989 B1 | 10/2002 | Yano et al. |
| 6,461,735 B1 | 10/2002 | Furuya et al. |
| 6,467,897 B1 | 10/2002 | Wu et al. |
| 6,468,500 B1 | 10/2002 | Sakaguchi et al. |
| 6,475,601 B1 | 11/2002 | Sakaki et al. |
| 6,479,150 B1 | 11/2002 | Liu et al. |
| 6,491,790 B1 | 12/2002 | Proverb et al. |
| 6,498,000 B2 | 12/2002 | Murasawa et al. |
| 6,517,199 B1 | 2/2003 | Tomioka et al. |
| 6,531,704 B2 | 3/2003 | Yadav et al. |
| 6,536,890 B1 | 3/2003 | Kato et al. |
| 6,548,264 B1 | 4/2003 | Tan et al. |
| 6,551,457 B2 | 4/2003 | Westman et al. |
| 6,562,441 B1 | 5/2003 | Maeda et al. |
| 6,575,383 B2 | 6/2003 | Dobler et al. |
| 6,578,521 B2 | 6/2003 | Raymond et al. |
| 6,589,562 B1 | 7/2003 | Shefer et al. |
| 6,607,711 B2 | 8/2003 | Pedersen |
| 6,623,848 B2 | 9/2003 | Brehm et al. |
| 6,638,918 B2 | 10/2003 | Davison et al. |
| 6,639,004 B2 | 10/2003 | Falat et al. |
| 6,645,569 B2 | 11/2003 | Cramer et al. |
| 6,680,279 B2 * | 1/2004 | Cai et al. .................... 502/327 |
| 6,693,071 B2 | 2/2004 | Ghosh et al. |
| 6,997,185 B2 * | 2/2006 | Han et al. .............. 128/204.17 |
| 7,008,979 B2 | 3/2006 | Schottman et al. |
| 7,141,518 B2 * | 11/2006 | MacDonald et al. .......... 442/59 |
| 2001/0000889 A1 | 5/2001 | Yadav et al. |
| 2001/0023338 A1 | 9/2001 | Guarracino et al. |
| 2001/0031248 A1 | 10/2001 | Hall-Puzio et al. |
| 2001/0056246 A1 | 12/2001 | Rodriguez-Fernandez et al. |
| 2002/0005145 A1 | 1/2002 | Sherman |
| 2002/0006425 A1 * | 1/2002 | Takaoka et al. ............. 424/405 |
| 2002/0066542 A1 | 6/2002 | Jakob et al. |
| 2002/0091071 A1 | 7/2002 | Fischer et al. |
| 2002/0106466 A1 | 8/2002 | Hausmann et al. |
| 2002/0110686 A1 | 8/2002 | Dugan |
| 2002/0128336 A1 | 9/2002 | Kolb et al. |
| 2002/0142937 A1 | 10/2002 | Carter et al. |
| 2002/0149656 A1 | 10/2002 | Nohr et al. |
| 2002/0150678 A1 | 10/2002 | Cramer et al. |
| 2002/0176982 A1 | 11/2002 | Rohrbaugh et al. |
| 2002/0177621 A1 | 11/2002 | Hanada |
| 2002/0182102 A1 | 12/2002 | Fontenot et al. |
| 2003/0013369 A1 | 1/2003 | Soane et al. |
| 2003/0021983 A1 | 1/2003 | Nohr et al. |
| 2003/0050211 A1 | 3/2003 | Hage et al. |
| 2003/0056648 A1 | 3/2003 | Fornai et al. |
| 2003/0070782 A1 | 4/2003 | Proverb et al. |
| 2003/0082237 A1 | 5/2003 | Cha et al. |
| 2003/0099718 A1 | 5/2003 | Burrell et al. |
| 2003/0100842 A1 | 5/2003 | Rosenberg et al. |
| 2003/0147956 A1 | 8/2003 | Shefer et al. |
| 2003/0147966 A1 | 8/2003 | Franzen et al. |
| 2003/0181540 A1 | 9/2003 | Quellet et al. |
| 2003/0203009 A1 | 10/2003 | MacDonald |
| 2003/0235605 A1 | 12/2003 | Lelah et al. |
| 2004/0033269 A1 | 2/2004 | Hei et al. |
| 2004/0034157 A1 | 2/2004 | Ghosh et al. |
| 2004/0043688 A1 | 3/2004 | Soerens et al. |
| 2005/0181067 A1 | 8/2005 | Yokoyama et al. |

FOREIGN PATENT DOCUMENTS

| | | |
|---|---|---|
| EP | 0251783 B1 | 1/1988 |
| EP | 0282287 B2 | 9/1988 |
| EP | 0339461 B1 | 11/1989 |
| EP | 0348978 A2 | 1/1990 |
| EP | 0376448 B1 | 7/1990 |
| EP | 0389015 A2 | 9/1990 |
| EP | 0389015 A3 | 9/1990 |
| EP | 0389023 A2 | 9/1990 |
| EP | 0389023 A3 | 9/1990 |
| EP | 0483500 A1 | 5/1992 |
| EP | 0510619 A1 | 10/1992 |
| EP | 0749295 B1 | 12/1996 |
| EP | 0972563 A1 | 1/2000 |
| EP | 1034800 A1 | 9/2000 |
| EP | 1157672 A1 | 11/2001 |
| EP | 1162172 A1 | 12/2001 |
| EP | 1188854 A1 | 3/2002 |
| EP | 1214878 A1 | 6/2002 |
| EP | 1216675 A1 | 6/2002 |
| EP | 1298071 A1 | 4/2003 |
| EP | 1315526 B1 | 6/2003 |
| EP | 1053788 B1 | 10/2003 |
| WO | WO 8902698 A1 | 4/1989 |
| WO | WO 9111977 A1 | 8/1991 |
| WO | WO 9112029 A1 | 8/1991 |
| WO | WO 9112030 A1 | 8/1991 |
| WO | WO 9619346 A2 | 6/1996 |
| WO | WO 9619346 A3 | 6/1996 |
| WO | WO 9725076 A1 | 7/1997 |
| WO | WO 9820915 A1 | 5/1998 |
| WO | WO 9826808 A2 | 6/1998 |
| WO | WO 9826808 A3 | 6/1998 |
| WO | WO 00/13764 A1 | 3/2000 |
| WO | WO 0076558 A1 | 12/2000 |
| WO | WO 0106054 A1 | 1/2001 |
| WO | WO 0226272 A1 | 4/2002 |
| WO | WO 02055115 A1 | 7/2002 |
| WO | WO 02062881 A2 | 8/2002 |
| WO | WO 02064877 A2 | 8/2002 |
| WO | WO 02064877 A3 | 8/2002 |
| WO | WO 02083297 A1 | 10/2002 |
| WO | WO 02084017 A1 | 10/2002 |
| WO | WO 02094329 A1 | 11/2002 |
| WO | WO 02095112 A1 | 11/2002 |
| WO | WO 03000979 A2 | 1/2003 |
| WO | WO 03025067 A1 | 3/2003 |
| WO | WO 03032959 A1 | 4/2003 |
| WO | WO 03088931 A2 | 10/2003 |
| WO | WO 03092885 A1 | 11/2003 |
| WO | WO 2004000986 A1 | 12/2003 |
| WO | WO 2004 060378 A2 | 7/2004 |

OTHER PUBLICATIONS

Abstract of Japanese Patent No. JP05098185, Apr. 20, 1993.
Abstract of Japanese Patent No. JP1262868, Oct. 19, 1989.
Abstract of Japanese Patent No. JP2157039, Jun. 15, 1990.
Abstract of Japanese Patent No. JP3195562, Aug. 27, 1991.
Abstract of Japanese Patent No. JP4335141, Nov. 24, 1992.
Abstract of Japanese Patent No. JP5261246, Oct. 12, 1993.
Abstract of Japanese Patent No. JP6285140, Oct. 11, 1994.
Abstract of Japanese Patent No. JP63072337, Apr. 2, 1988.
Abstract of Japanese Patent No. JP8152409, Jun. 11, 1996.
Abstract of SU834073, May 30, 1981.
Abstract of Japanese Patent No. 7256025, Oct. 9, 1995.
Abstract of Japanese Patent No. 5106199, Apr. 27, 1993.
Abstract of Japanese Patent No. 9143872, Jun. 3, 1997.

*Applicability of a SPME method for the Rapid Determination of VOCs*, Alexandre Béné, Jean-Luc Luisier, and Antoine Fornage, Chimia, vol. 56, No. 6, 2002, pp. 289-291.

*Characterisation of novel modified active carbons and marine algal biomass for the selective adsorption of lead*, D.J. Malik, V. Strelko, Jr., M. Streat, and A.M. Puziy, Water Research, vol. 36, 2002, pp. 1527-1538.

*Significance of Ammonia in the Genesis of Gastric Epithelial Lesions Induced by Helicobacter pylori: An in vitro Study with Different Bacterial Strains and Ureo Concentrations*, P. Sommi, V. Ricci, R. Fiocca, M. Romano, K.J. Ivey, E. Cova, E. Solcia, and U. Ventura, Digestion, vol. 57, 1996, pp. 299-304.

*Ammonia vapour in the mouth as a diagnostic marker for Helicobacter pylori infection: preliminary "proof of principle" pharmacological investigations*, C. D. R. Dunn, M. Black, D. C. Cowell, C. Penault, N. M. Ratcliffe, R. Spence, and C. Teare, British Journal of Biomedical Science, vol. 58, 2001, pp. 66-76.

*Purification and Characterization of Urease from Helicobacter pylori*, Bruce E. Dunn, Gail P. Campbell, Guillermo I. Perez-Perez, and Martin J. Blaser, The Journal of Biological Chemistry, vol. 265, No. 16, Jun. 5, 1990, pp. 9464-1990.

*Validation of $^{13}$C-Urea Breath Test for the Diagnosis of Helicobacter Pylori Infection in the Singapore Population*, T. S. Chua, K. M. Fock, E. K. Teo, T. M. Ng, Singapore Medical Journal, vol. 43, No. 8, 2002, pp. 408-411.

*Significance of ammonia produced by Helicobacter pylori*, Shigeji Ito, Yoshihiro Kohli, Takuji Kato, Yoshimichi Abe, and Takashi Ueda, European Journal of Gastroenterology & Hepatology, vol. 6, No. 2, 1994, pp. 167-174.

*Spectrophotometric Assay of Thiols*, Peter C. Jocelyn, Methods in Enzymology, vol. 142, 1987, pp. 44-67.

*Adsorption of Dyes on Nanosize Modified Silica Particles*, Guangwei Wu, Athanasia Koliadima, Yie-Shein Her, and Egon Matijevic, Journal of Colloid and Interface Sciences, vol. 195, 1997, pp. 222-228.

*Adsorption of Proteins and Antibiotics on Porous Alumina Membranes*, Yi Hua Ma, Aseem Bansal, and William M. Clark, Fundamentals of Adsorption, vol. 80, 1992, pp. 389-396.

*Saponins and Sapogenins. VIII. Surface Films of Echinocystic Acid and Derivatives*, C. R Noller, J. Am. Chem. Soc., vol. 60, 1938, 3 pages.

*Immobilization of $(n-Bu_4N)_4W_{10}O_{32}$ on Mesoporous MCM-41 and Amorphous Silicas for Photocatalytic Oxidation of Cycloalkanes with Molecular Oxygen*, Andrea Maldotti, Alessandra Molinari, Graziano Varani, Maurizio Lenarda, Loretta Storaro, Franca Bigi, Raimondo Maggi, Alessandro Mazzacani, and Giovanni Sartori, Journal of Catalysis, vol. 209, 2002, pp. 210-216.

*Fe-MCM-41 for Selective Epoxidation of Styrene with Hydrogen Peroxide*, Qinghong Zhang, Ye Wang, Satoko Itsuki, Tetsuya Shishido, and Katsuomi Takehira, The Chemical Society of Japan, Chemistry Letters 2001, pp. 946-947.

*Mesoporous Sieves with Unified Hybrid Inorganic/Organic Frameworks*, Brian J. Melde, Brian T. Holland, Christopher F. Blanford, and Andreas Stein, Chem. Mater., vol. 11, No. 11, 1999, pp. 3302-3308.

*From Cyclodextrin Assemblies to Porous Materials by Silica Templating*, Sebastian Polarz, Bernd Smarsly, Lyudmila Bronstein, and Markus Antonietti, Angew. Chem. Int., vol. 40, No. 23, 2001, pp. 4417-4421.

*Uniform Deposition of Ultrathin Polymer Films on the Surfaces of $Al_2O_3$ Nanoparticles by a Plasma Treatment*, Donglu Shi, S. X. Wang, Wim J. van Ooij, L. M. Wang, Jiangang Zhao, and Zhou Yu, University of Cincinnati and University of Michigan, Jun. 2000, pp. 1-15.

*Development of novel dye-doped silica nanoparticles for biomarker application*, Swadeshmukul Santra, Kemin Wang, Rovelyn Tapec, and Weihong Tan, Journal of Biomedical Optics, vol. 6, No. 2, Apr. 2001, pp. 160-166.

*Nanoparticles based on polyelectrolyte complexes: effect of structure and net charge on the sorption capability for solved organic molecules*, H.-M. Buchhammer, G. Petzold, and K. Lunkwitz, Colloid Polym. Sci., vol. 278, 2000, pp. 841-847.

*Adsorption of Gases in Multimolecular Layers*, Stephen Brunauer, P.H. Emmett, and Edward Teller, The Journal of the American Chemical Society, vol. 60, Feb. 1938, pp. 309-319.

*Study of the urea thermal decomposition (pyrolysis) reaction and importance to cyanuric acid production*, Peter M. Schaber, James Colson, Steven Higgins, Ed Dietz, Daniel Thielen, Bill Anspach, and Jonathan Brauer, American Laboratory, Aug. 1999, pp. 13-21.

*The Colloid Chemistry of Silica*, American Chemical Society 200$^{th}$ National Meeting, Aug. 26-31, 1990, pp. 22-23 and pp. 52-59.

*Structure and properties of silica nanoclusters at high temperatures*, I. V. Schweigert, K. E. J. Lehtinen, M. J. Carrier, and M. R. Zachariah, The American Physical Society, Physical Review B, vol. 65. No. 235410, pp. 1-9, 2002.

*Grafting of Poly(ethylenimine) onto Mesylated Cellulose Acetate, Poly(methyl methacrylate) and Poly(vinyl chloride)*, Christopher J. Biermann and Ramani Narayan, Carbohydrate Polymers, vol. 12, 1990, pp. 323-327.

Abstract *Non-hydrothermal synthesis of coper-,-zinc- and copper-zinc hydrosilicates*, T. M. Yurieva, G. N. Kustova, T. P. Minyukova, E. K. Poels, A. Bliek, M. P. Demeshkina, L. M. Plyasova, T. A. Krieger, and V. I. Zaikovskii, Materials Research Innovations, vol. 5, No. 1, Jun. 2001, pp. 3-11.

Pocket Guide to Digital Printing, Frank Cost, Delmar Publishers, Albany, NY, ISBN 0-8273-7592-1, pp. 144-145, 1999.

Article—*Immunization of mice with peptomers covalently couopled to aluminum oxide nanoparticles*, Andreas Frey, Nicholas Mantis, Pamela A. Kozlowski, Alison J. Quayle, Adriana Bajardi, Juana J. Perdomo, Frank A. Robey, and Marian R. Neutra, Vaccine, vol. 17, 1999, pp. 3007-3019.

* cited by examiner

METHOD FOR REDUCING ODOR USING COLLOIDAL NANOPARTICLES

BACKGROUND OF THE INVENTION

Odor control additives have been conventionally incorporated into substrates for a variety of reasons. For instance, U.S. Pat. No. 6,225,524 to Guarracino, et al. describes a substrate having an odor control composition that includes an absorbent gelling material and silica. Likewise, U.S. Pat. No. 6,376,741 to Guarracino, et al. describes a substrate having an odor control composition that includes silica and a zeolite (i.e., crystalline aluminosilicate). For instance, one type of silica said to be preferred in Guarracino, et al. ('524 patent) is amorphous silica having a particle size of 4-12 microns and a pore volume of 1-2 g/ml. Another type of preferred silica is said to be a silica gel having a medium pore diameter of from 90 to 110 angstroms, a surface area of from 250 $m^2$/g to 350 $m_2$/g, and an average particle size of from 63 to 200 microns.

Unfortunately, conventional odor control compositions, such as described above, have proven ineffective in obtaining the full level of odor control desired in many applications. For example, most conventional silica has a relatively large average size (i.e., micron scale). This large size results in a coating with a small available surface area for contacting the odorous compound, and may in fact reduce the porosity of a substrate to which it is applied. The large size of the particles also allows them to be easily rubbed off of the substrate, which results in a reduction in the coating over time. The porosity of some types of conventional silica may also reduce uniformity and stability.

As such, a need exists for an odor control composition that may exhibit improved odor control properties, particularly when applied to a substrate.

SUMMARY OF THE INVENTION

In accordance with one embodiment of the present invention, a method for reducing odor is disclosed. The method comprises contacting a substrate containing a thin coating of colloidal nanoparticles with an odorous compound. The colloidal nanoparticles may be formed, for instance, from a material selected from the group consisting of silica, alumina, zirconia, magnesium oxide, titanium dioxide, iron oxide, zinc oxide, copper oxide, organic compounds, and combinations thereof. Particular examples of the nanoparticles include, silica nanoparticles (with or without coating of alumina) and alumina nanoparticles. The colloidal nanoparticles have an average size of less than about 100 nanometers, in some embodiments from about 1 to about 50 nanometers, and in some embodiments, from about 4 to about 20 nanometers. The colloidal nanoparticles also have a surface area of from about 50 to about 1000 square meters per gram, and in some embodiments, from about 100 to about 600 square meters per gram. In addition, the colloidal nanoparticles may be solid, e.g., have a pore volume of less than about 0.5 milliliters per gram, in some embodiments less than about 0.4 milliliters per gram, and in some embodiments, less than about 0.3 milliliters per gram.

The colloidal nanoparticles may be applied to the substrate in a variety of ways, such as applied to the surface of the substrate or incorporated into the matrix of the substrate. For example, in some embodiments, the colloidal nanoparticles may cover at least about 50% of a surface of the substrate, in some embodiments, at least about 80% of a surface of the substrate, and in some embodiments, approximately 100% of a surface of the substrate. The solids add-on level of the colloidal nanoparticles may also constitute be from about 0.001% to about 20%, in some embodiments from about 0.01% to about 10%, and in some embodiments, from about 0.1% to about 4%. When coated onto the substrate, the thickness of the coating may also be less than about 1 micron, in some embodiments from about 2 to about 500 nanometers, and in some embodiments, from about 4 to about 200 nanometers. If desired, the substrate may maintain a certain porosity after application of the colloidal nanoparticles. For instance, in some embodiments, the substrate may have a porosity such that from about 20 to about 500 cubic feet of air is capable of flowing through 1 square foot of the substrate per minute under a pressure differential of 125 Pascals.

The present inventors have discovered that the colloidal nanoparticles may adsorb at least about 25%, in some embodiments at least about 45%, and in some embodiments, at least about 65% of an odorous compound when contacted therewith. Some examples of odorous compounds that may adsorbed by the colloidal nanoparticles include, but are not limited to, mercaptans, ammonia, amines, sulfides, ketones, carboxylic acids, aldehydes, terpenoids, hexanol, heptanal, pyridine, and combinations thereof.

In accordance with another embodiment of the present invention, a substrate for reducing odor is disclosed. The substrate is porous and comprises a nonwoven, woven, or paper web. The substrate also contains having an average size of from about 1 to about 50 nanometers, a surface area of from about 50 to about 1000 square meters per gram, and a pore volume of less than about 0.4 milliliters per gram. In one embodiment, the substrate may be incorporated into an absorbent article that includes a liquid-transmissive liner, a liquid-transmissive surge layer, a liquid-absorbent core, and a vapor-permeable, and/or a liquid-impermeable outer cover, where the substrate forms at least a portion of the liner, surge layer, absorbent core, outer cover, or combinations thereof. In another embodiment, the substrate may be incorporated into a paper product, such as a bath tissue, facial tissue, paper towel, etc., or a facemask.

Other features and aspects of the present invention are discussed in greater detail below.

DETAILED DESCRIPTION OF REPRESENTATIVE EMBODIMENTS

Definitions

As used herein, an "absorbent article" refers to any article capable of absorbing water or other fluids. Examples of some absorbent articles include, but are not limited to, personal care absorbent articles, such as diapers, training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth. Materials and processes suitable for forming such absorbent articles are well known to those skilled in the art.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc.

As used herein, the term "meltblowing" refers to a process in which fibers are formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonding" refers to a process in which small diameter substantially continuous fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

In general, the present invention is directed to colloidal nanoparticles configured to reduce various types of odors. "Colloidal" nanoparticles refer to nanoparticles that may exist as a stable liquid dispersion. The colloidal nanoparticles of the present invention may possess various forms, shapes, and sizes depending upon the desired result. For instance, the colloidal nanoparticles may be in the shape of a sphere, crystal, rod, disk, tube, string, etc. The average size of the colloidal nanoparticles is generally less than about 100 nanometers, in some embodiments from about 1 to about 50 nanometers, in some embodiments from about 2 to about 50 nanometers, and in some embodiments, from about 4 to about 20 nanometers. As used herein, the average size of a particle refers to its average length, width, height, and/or diameter.

The colloidal nanoparticles may have a surface area of from about 50 square meters per gram ($m^2/g$) to about 1000 $m^2/g$, in some embodiments from about 100 $m^2/g$ to about 600 $m^2/g$, and in some embodiments, from about 180 $m^2/g$ to about 240 $m^2/g$. Surface area may be determined by the physical gas adsorption (B.E.T.) method of Bruanauer, Emmet, and Teller, Journal of American Chemical Society, Vol. 60, 1938, p. 309, with nitrogen as the adsorption gas. In addition, the colloidal nanoparticles may also be relatively nonporous or solid. That is, the colloidal nanoparticles may have a pore volume that is less than about 0.5 milliliters per gram (ml/g), in some embodiments less than about 0.4 milliliters per gram, in some embodiments less than about 0.3 ml/g, and in some embodiments, from about 0.2 ml/g to about 0.3 ml/g. Without intending to be limited by theory, it is believed that colloidal nanoparticles having such a small size and high surface area may improve the adsorption capability of the nanoparticles for many odorous compounds. Moreover, it is believed that the solid nature, i.e., low pore volume, of the colloidal nanoparticles may enhance the uniformity and stability of the nanoparticles, without sacrificing its odor adsorption characteristics.

The colloidal nanoparticles may be formed from a variety of materials, including, but not limited to, silica, alumina, zirconia, magnesium oxide, titanium dioxide, iron oxide, zinc oxide, copper oxide, organic compounds such as polystyrene, and combinations thereof. For example, alumina nanoparticles may be used for odor reduction in accordance with certain embodiments of the present invention. Some suitable alumina nanoparticles are described in U.S. Pat. No. 5,407,600 to Ando, et al., which is incorporated herein in its entirety by reference thereto for all purposes. Further, examples of commercially available alumina nanoparticles include, for instance, Aluminasol 100, Aluminasol 200, and Aluminasol 520, which are available from Nissan Chemical Industries Ltd. Alternatively, in other embodiments, silica nanoparticles may be utilized, such as Snowtex-C, Snowtex-O, Snowtex-PS, and Snowtex-OXS, which are also available from Nissan Chemical. Snowtex-OXS particles, for instance, have a particle size of from 4 to 6 nanometers, and may be ground into a powder having a surface area of approximately 509 square meters per gram. Also, alumina-coated silica particles may be used, such as Snowtex-AK available from Nissan Chemical.

Colloidal nanoparticles, such as referenced above, may possess units that may or may not be joined together. Whether or not such units are joined generally depends on the conditions of polymerization. For instance, when forming silica nanoparticles, the acidification of a silicate solution may yield $Si(OH)_4$. If the pH of this solution is reduced below 7 or if a salt is added, then the units may tend to fuse together in chains and form a "silica gel." On the other hand, if the pH is kept at a neutral pH or above 7, the units may tend to separate and gradually grow to form a "silica sol." Such colloidal silica nanoparticles may generally be formed according to any of a variety of techniques well known in the art, such as dialysis, electrodialysis, peptization, acid neutralization, and ion exchange. Some examples of such techniques are described, for instance, in U.S. Pat. No. 5,100,581 to Watanabe, et al.; U.S. Pat. No. 5,196,177 to Watanabe, et al.; U.S. Pat. No. 5,230,953 to Tsugeno, et al. and U.S. Pat. No. 5,985,229 to Yamada, et al., which are incorporated herein in their entirety by reference thereto for all purposes.

In one particular embodiment, a silica nanoparticle sol is formed using an ion-exchange technique. For exemplary purposes only, one such ion-exchange technique will now be described in more detail. Initially, an alkali metal silicate is provided that has a molar ratio of silicon ($SiO_2$) to alkali metals ($M_2O$) of from about 0.5 to about 4.5. For instance, sodium water glass may be utilized that has a molar ratio of from about 2 to about 4. An aqueous solution of the alkali metal silicate is obtained by dissolving it in water at a concentration of, for instance, from about 2 wt. % to about 6 wt. %. The alkali metal silicate-containing aqueous solution may then be contacted with one or more ion-exchange resins. For instance, the solution may first be contacted with a strong-acid to ion-exchange all the metal ions in the aqueous solution. Examples of such strong acids include, but are not limited to, hydrochloric acid, nitric acid, sulfuric acid, and so forth. The contact may be accomplished by passing the aqueous solution through a column filled with the strong acid at a temperature of from about 0° C. to about 60° C., and in some embodiments, from about 5° C. to about 50° C. After passing through the column, the resulting silicic acid-containing aqueous solution may have a pH value of from about 2 to about 4. If desired, another strong acid may be added to the silicic acid-containing aqueous solution to convert the impurity metal components into dissociated ions. This additional strong acid may decrease the pH value of the resulting solution to less than about 2, and in some embodiments, from about 0.5 to about 1.8.

The metal ions and the anions from the strong acid may be removed from the solution by consecutive application of a strong acid (i.e., cation-exchange resin) and strong base (anion-exchange resin). Examples of suitable strong bases include, but are not limited to, sodium hydroxide, potassium hydroxide, and so forth. As a result of this consecutive application, the silicic acid-containing aqueous solution may have a pH value of from about 2 to about 5. This acidic aqueous solution may then be contacted with one or more additional strong bases to stabilize the solution at a pH value of from about 7 to about 9.

The stabilized silicic acid-containing aqueous solution is then fed to a container in which the liquid temperature is maintained at from about 70° C. to about 100° C. This process results in an increase in concentration of the silica to from about 30 wt. % to about 50 wt. %. The stable aqueous silica sol may then be consecutively contacted with a strong acid and strong base, such as described above, so that the resulting aqueous silica sol is substantially free from polyvalent metal oxides, other than silica. Finally, ammonia may be added to the aqueous sol to further increase its pH value to from about 8 to about 10.5, thereby forming a stable aqueous silica sol having a silica concentration of from about 30 wt. % to about 50 wt. %, a mean particle size of from about 10 to about 30 nanometers, and that is substantially free from any polyvalent metal oxides, other than silica.

The colloidal nanoparticles of the present invention, such as described above, may be used in various applications to reduce a variety of different types of odors. For instance, the colloidal nanoparticles may be useful in removing odorous compounds, such as mercaptans (e.g., ethyl mercaptan), ammonia, amines (e.g., trimethylamine (TMA), triethylamine (TEA), etc.), sulfides (e.g., hydrogen sulfide, dimethyl disulfide (DMDS), etc.), ketones (e.g., 2-butanone, 2-pentanone, 4-heptanone, etc.) carboxylic acids (e.g., isovaleric acid, acetic acid, propionic acid, etc.), aldehydes, terpenoids, hexanol, heptanal, pyridine, and combinations thereof.

If desired, the colloidal nanoparticles of the present invention may be applied to a substrate. The substrate may provide an increased surface area to facilitate the adsorption of odorous compounds by the colloidal nanoparticles. In addition, the substrate may also serve other purposes, such as water absorption. Any of a variety of different substrates may be incorporated with the colloidal nanoparticles in accordance with the present invention. For instance, nonwoven fabrics, woven fabrics, knit fabrics, paper, film, foams, etc., may be applied with the colloidal nanoparticles. When utilized, the nonwoven fabrics may include, but are not limited to, spunbonded webs (apertured or non-apertured), meltblown webs, bonded carded webs, air-laid webs, coform webs, hydraulically entangled webs, and so forth.

In some embodiments, for example, the colloidal nanoparticles may be utilized in a paper product containing one or more paper webs, such as facial tissue, bath tissue, paper towels, napkins, and so forth. The paper product may be single-ply in which the web forming the product includes a single layer or is stratified (i.e., has multiple layers), or multi-ply, in which the webs forming the product may themselves be either single or multi-layered. Normally, the basis weight of such a paper product is less than about 120 grams per square meter (gsm), in some embodiments less than about 80 gsm, in some embodiments less than about 60 grams per square meter, and in some embodiments, from about 10 to about 60 gsm.

Any of a variety of materials can also be used to form the paper web(s) of the product. For example, the material used to make the paper product may include fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable for the present invention include those available from Kimberly-Clark Corporation under the trade designations "Longlac-19". Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabai grass, milkweed floss, pineapple leaf, and so forth. In addition, in some instances, synthetic fibers can also be utilized. Some suitable synthetic fibers can include, but are not limited to, rayon fibers, ethylene vinyl alcohol copolymer fibers, polyolefin fibers, polyesters, and so forth.

If desired, the substrate may form all or a portion of an absorbent article. In one embodiment, for instance, the absorbent article includes a liquid-transmissive bodyside liner, a liquid-transmissive surge layer below the bodyside liner, a liquid-absorbent core below the surge layer, and a moisture vapor permeable, liquid impermeable outer cover below the absorbent core. A substrate treated with the colloidal nanoparticles of the present invention may be employed as any one or more of the liquid transmissive (non-retentive) and absorbent layers. An absorbent core of the absorbent article, for instance, may be formed from an absorbent nonwoven web that includes a matrix of hydrophilic fibers. In one embodiment, the absorbent web may contain a matrix of cellulosic fluff fibers. One type of fluff that may be used in the present invention is identified with the trade designation CR1654, available from U.S. Alliance, Childersburg, Ala., U.S.A., and is a bleached, highly absorbent sulfate wood pulp containing primarily soft wood fibers. In another embodiment, the absorbent nonwoven web may contain a hydoentangled web. Hydroentangling processes and hydroentangled composite webs containing various combinations of different fibers are known in the art. A typical hydroentangling process utilizes high pressure jet streams of water to entangle fibers and/or filaments to form a highly entangled consolidated fibrous structure, e.g., a nonwoven fabric. Hydroentangled nonwoven fabrics of staple length fibers and continuous filaments are disclosed, for example, in U.S. Pat. No. 3,494,821 to Evans and U.S. Pat. No. 4,144,370 to Bouolton, which are incorporated herein in their entirety by reference thereto for all purposes. Hydroentangled composite nonwoven fabrics of a continuous filament nonwoven web and a pulp layer are disclosed, for example, in U.S. Pat. No. 5,284,703 to Everhart, et al. and U.S. Pat. No. 6,315,864 to Anderson, et al., which are incorporated herein in their entirety by reference thereto for all purposes.

Another type of suitable absorbent nonwoven web is a coform material, which is typically a blend of cellulose fibers and meltblown fibers. The term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

If desired, the absorbent nonwoven web may also contain a superabsorbent material. Superabsorbents have the ability to absorb a great amount of fluid in relation to their own weight. Typical superabsorbents used in sanitary napkins may absorb anywhere from about 5 to about 60 times their weight in blood. Superabsorbent materials are produced in a wide variety of forms including, but not limited to, particles, fibers and flakes. Superabsorbents having a high mechanical stability in the swollen state, an ability to rapidly absorb fluid, and those having a strong liquid binding capacity, typically perform well in absorbent articles. Hydroxyfunctional polymers have been found to be good superabsorbents for this application. For example, a hydrogel-forming polymer, such as a partially neutralized cross-linked copolymer of polyacrylic acid and polyvinyl alcohol, may be utilized. After the polymer is formed, it is mixed with about a 1% anhydrous citric acid powder. The citric acid has been found to increase the ability of the superabsorbent to absorb menses and blood. This is particularly beneficial for use in a sanitary napkin or other feminine pads. The finely ground, anhydrous citric acid powder, which is void of water, along with trace amounts of fumed silica, is mixed with the polymer that may have been screened to an appropriate particle size. This mixture may also be formed into a composite or a laminate structure. Such superabsorbents may be obtained from Dow Chemical and Stockhausen, Inc., among others. This superabsorbent is a partially neutralized salt of cross-linked copolymer of polyacrylic acid and polyvinyl alcohol having an absorbency under load value above about 25. Some suitable superabsorbents are described in U.S. Pat. No. 4,798,603 to Meyers, et al., U.S. Pat. No. Re. 32,649 to Brandt, et al. and U.S. Pat. No. 4,467,012 to Pedersen, et al., U.S. Pat. Nos. 4,604,313 and 4,655,757 to McFarland, et al., U.S. Pat. No. 6,387,495 to Reeves, et al., as well as in published European Patent Application 0,339,461 to Kellenberger.

As indicated above, the colloidal nanoparticles may also be applied to a liquid transmissive layer of the absorbent article, such as the bodyside liner or surge layer. Such liquid transmissive layers are typically intended to transmit liquid quickly, and thus generally do not retain or absorb significant quantities of aqueous liquid. Materials that transmit liquid in such a manner include, but are not limited to, thermoplastic spunbonded webs, meltblown webs, bonded carded webs, air laid webs, and so forth. A wide variety of thermoplastic materials may be used to construct these non-retentive nonwoven webs, including without limitation polyamides, polyesters, polyolefins, copolymers of ethylene and propylene, copolymers of ethylene or propylene with a $C_4$-$C_{20}$ alpha-olefin, terpolymers of ethylene with propylene and a $C_4$-$C_{20}$ alpha-olefin, ethylene vinyl acetate copolymers, propylene vinyl acetate copolymers, styrene-poly(ethylene-alpha-olefin) elastomers, polyurethanes, A-B block copolymers where A is formed of poly(vinyl arene) moieties such as polystyrene and B is an elastomeric midblock such as a conjugated diene or lower alkene, polyethers, polyether esters, polyacrylates, ethylene alkyl acrylates, polyisobutylene, poly-1-butene, copolymers of poly-1-butene including ethylene-1-butene copolymers, polybutadiene, isobutylene-isoprene copolymers, and combinations of any of the foregoing.

The amount of the colloidal nanoparticles present on the substrate may vary depending on the nature of the substrate and its intended application. In some embodiments, for example, the dry, solids add-on level is from about 0.001% to about 20%, in some embodiments from about 0.01% to about 10%, and in some embodiments, from about 0.1% to about 4%. The "solids add-on level" is determined by subtracting the weight of the untreated substrate from the weight of the treated substrate (after drying), dividing this calculated weight by the weight of the untreated substrate, and then multiplying by 100%. Lower add-on levels may provide optimum absorbency or other characteristics of the substrate, while higher add-on levels may provide optimum odor reduction.

The colloidal nanoparticles may be applied to a substrate using any of a variety of well-known application techniques. Suitable techniques for applying the composition to a substrate include printing, dipping, spraying, melt extruding, solvent coating, powder coating, and so forth. The colloidal nanoparticles may be incorporated within the matrix of the substrate and/or applied to the surface thereof. For example, in one embodiment, the colloidal nanoparticles are coated onto one or more surfaces of the substrate. When coated onto the substrate, the resulting thickness of the coating may be minimal so that it is almost invisible to the naked eye. For instance, the thickness of the coating may be less than about 1 micron, in some embodiments from about 2 to about 500 nanometers, and in some embodiments, from about 4 to about 200 nanometers.

The percent coverage of the colloidal nanoparticles on the surface may be selected to achieve the desired odor reduction. Typically, the percent coverage is greater than about 50%, in some embodiments greater than about 80%, and in some embodiments, approximately 100% of the area of a given surface. The present inventors have discovered that, even when applied uniformly (e.g., about 100% coverage) onto a surface of the substrate, the resulting substrate may still remain porous. Specifically, without intending to be limited by theory, it is believed that the small size of the colloidal nanoparticles limits their ability to block the pores of the substrate. In addition, it is also believed that the solid nanoparticles aggregate in such a manner that a coating of the nanoparticles is actually considered porous.

Thus, in some instances, a substrate containing the nanoparticle coating may remain porous to provide a variety of benefits. For instance, the porosity of the coated substrate may enable it to still be used in application where liquid permeability is required, such as in absorbent articles. Also, the porosity of the coated substrate allows gaseous odorous compounds to flow therethrough, exposing the underside of the nanoparticles (surface of nanoparticles facing the substrate) to the odorous compound. In this manner, the entire surface area of the nanoparticles is more effectively utilized for reducing odor. In most embodiments, the coated substrate exhibits a porosity such that about 20 cubic feet of air or greater may flow through 1 square foot of the substrate in 1 minute under an air pressure differential of 125 Pascals (0.5 inches of water). In other words, such a substrate is said to have an air permeability of about 20 cubic feet per minute (cfm) or greater. In some embodiments, the air permeability ranges from about 20 cfm to about 500 cfm, in some embodiments from about 50 cfm to about 400 cfm, and in some embodiments, from about 75 cfm to about 300 cfm, under an air pressure differential of 125 Pascals. Air permeability (volumetric air flow per square foot of material under an air pressure differential of 125 Pascals) may be measured in a variety of ways. For example, "Frazier Air Permeability" is determined according to Federal Test Standard 191A, Method 5450 with a Frazier Air Permeability Tester (Frazier Precision Instrument Co., Gaithersburg, Md.), and is reported as an average of 3 sample readings.

The colloidal nanoparticles of the present invention are versatile and may also be used with other types of articles of manufacture. For instance, the colloidal nanoparticles may be used in air filters, such as house filters, vent filters, disposable facemasks, and facemask filters. Exemplary facemasks, for instance, are described and shown, for example, in U.S. Pat. Nos. 4,802,473; 4,969,457; 5,322,061; 5,383,450; 5,553,608; 5,020,533; 5,813,398; and 6,427,693, which are incorporated herein in their entirety by reference thereto for all purposes. In one embodiment, a substrate coated with the colloidal nanoparticles of the present invention may be utilized as a filtration layer of the facemask. Filtration layers, such as meltblown nonwoven webs, spunbond nonwoven webs, and laminates thereof, are well known in the art.

In another embodiment, the colloidal nanoparticles may be applied to walls, wallpaper, glass, toilets, and/or countertops. For instance, the colloidal nanoparticles may be used in a restroom facility. Other uses include, without limitation, refrigerator mats and fabric softener sheets.

The colloidal nanoparticles may also be applied to water treatment systems for removing sulphurous compounds from well water or in toilet tanks to reduce the odors resulting from urine. The colloidal nanoparticles may also be used in liquid detergents and household cleaners to remove odors. In another embodiment, the nanoparticles are used as aerosol odor neutralizers/deodorants. The colloidal nanoparticles are packaged with a propellant that allows spraying the colloidal nanoparticles into the air for removal of gases and odorous compounds. The colloidal nanoparticles may be used in a household air freshener or be used in combination with a mist emitted from a vaporizer or humidifier.

The effectiveness of the colloidal nanoparticles of the present invention may be measured in a variety of ways. For example, the percent of an odorous compound adsorbed by the colloidal nanoparticles may be determined in accordance with the headspace gas chromatography test set forth herein. In some embodiments, for instance, the colloidal nanoparticles of the present invention are capable of adsorbing at least about 25%, in some embodiments at least about 45%, and in some embodiments, at least about 65% of a particular odorous compound. The effectiveness of the colloidal nanoparticles in removing odors may also be measured in terms of "Relative Adsorption Efficiency", which is also determined using headspace gas chromatography. For instance, the "Relatively Adsorption Efficiency" of acetaldehyde may be at least about 25 milligrams of acetaldehyde adsorbed per gram of the substrate (mg/g), and in some embodiments, at least about 35 mg/g. In addition, the "Relatively Adsorption Efficiency" of 2,3 butanedione may be at least about 300 milligrams of 2,3 butanedione adsorbed per gram of the substrate (mg/g). It should be recognized that the surface chemistry of any one type of nanoparticle may not be suitable to reduce all types of odors, and that low adsorption of one or more odorous compounds may be compensated by good adsorption of other odorous compounds.

Thus, as a result of the present invention, a substrate may be applied with a very thin coating of colloidal nanoparticles having excellent odor adsorption characteristics. Because the coating is porous, odorous compounds readily flow through the coating and substrate, thereby optimizing their contact with the surface area of the nanoparticles. In this manner, small amounts of colloidal nanoparticles may still achieve high levels of odor reduction.

The present invention may be better understood with reference to the following examples.

Test Method

Odor adsorption was determined in the Example using a test known as "Headspace Gas Chromatography." Headspace gas chromatography testing was conducted on an Agilent Technologies 5890, Series II gas chromatograph with an Agilent Technology 7694 headspace sampler (Agilent Technologies, Waldbronn, Germany). Helium was used as the carrier gas (injection port pressure: 12.7 psig; headspace vial pressure: 15.8 psig; supply line pressure is at 60 psig). A DB-624 column was used for the odorous compound that had a length of 30 meters and an internal diameter of 0.25 millimeters. Such a column is available from J&W Scientific, Inc. of Folsom, Calif.

The operating parameters used for the headspace gas chromatography are shown below in Table 1:

TABLE 1

Operating Parameters for the Headspace Gas Chromatography Device.
Headspace Parameters

| | | |
|---|---|---|
| Zone Temps, ° C. | Oven | 37 |
| | Loop | 42 |
| | TR. Line | 47 |
| Event Time, minutes | GC Cycle time | 10.0 |
| | Vial eq. Time | 10.0 |
| | Pressuriz. Time | 0.20 |
| | Loop fill time | 0.20 |
| | Loop eq. Time | 0.15 |
| | Inject time | 0.30 |
| Vial Parameters | First vial | 1 |
| | Last vial | 1 |
| | Shake | [off] |

The test procedure involved placing 0.005-0.006 gram of the sample in a 20-cubic centimeter headspace vial. Using a syringe, an aliquot of the odorous compound was also placed in the vial. The vial was then sealed with a cap and a septum and placed in the headspace gas chromatography oven at 37° C. After ten minutes, a hollow needle was inserted through the septum and into the vial. A 1-cubic centimeter sample of the headspace (air inside the vial) was then injected into the gas chromatograph. Initially, a control vial with only the aliquot of odorous compound was tested to define 0% odorous compound adsorption. To calculate the amount of headspace odorous compound removed by the sample, the peak area for the odorous compound from the vial with the sample was compared to the peak area from the odorous compound control vial. Testing was done with 5 microliters of 2,3-butanedione, 5 microliters of acetaldehyde, and 5 microliters of 3-methyl butanal. Each sample was tested in duplicate.

EXAMPLE 1

The effectiveness of the colloidal nanoparticles to adsorb odorous compounds was demonstrated. Three types of colloidal silica nanoparticles were tested. Specifically, the colloidal silica nanoparticles were Snowtex-PS, Snowtex-O, and Snowtex-C, all of which are commercially available from Nissan Chemical America of Houston, Tex. The particles had an average particle size of between 10 to 20 nanometers, a surface area between 180 to 240 square meters per gram, and were present at approximately 20 wt. % solids in the solution. The Snowtex-C suspension was diluted to a 5 wt. % solids solution by adding deionized water while stirring for 10 minutes. The suspension was then poured into a shallow dish. A Kimwipe® wiper, which is a 1-ply cellulosic tissue wiper available from Kimberly-Clark Corporation, was dipped into the dish and then allowed to air dry on the sash of a fume hood. After drying, the add-on level was approximately 2.4%.

The samples were then tested for odor adsorption as described above. The results are shown below in Tables 2-4 in terms of milligrams of the odorous compound removed per gram of sample, i.e., relative adsorption efficiency, and percent odor removed.

TABLE 2

Removal of Acetaldehyde

| Sample | Relative Adsorption Efficiency (mg odor removed/g sample) | % Odor removed |
|---|---|---|
| Snowtex-PS | 35 | 46 |
| Snowtex-O | 36 | 65 |
| Snowtex-C | 90 | 22 |

TABLE 3

Removal of 2,3 Butanedione

| Sample | Relative Adsorption Efficiency (mg odor removed/g sample) | % Odor removed |
|---|---|---|
| Snowtex-C | 372 | 78 |

TABLE 4

Removal of 3-Methyl Butanal

| Sample | Relative Adsorption Efficiency (mg odor removed/g sample) | % Odor removed |
|---|---|---|
| Snowtex-C | 90 | 22 |

As indicated, the colloidal silica nanoparticles were capable of effectively adsorbing aldehyde and ketone odors when contained on a substrate.

EXAMPLE 2

The effectiveness of the colloidal nanoparticles to adsorb odorous compounds was demonstrated. Two types of colloidal nanoparticles were tested. Specifically, the colloidal nanoparticles were Snowtex-C and Snowtex-AK, all of which are commercially available from Nissan Chemical America of Houston, Tex. The particles had an average particle size of between 10 to 20 nanometers, a surface area between 180 to 240 square meters per gram, and were present at approximately 20 wt. % solids in the solution. 10 milliliters of the colloidal silica nanoparticles were dried at 80° C. to form powders that were then ground to a surface area of 220 square meters per gram. The powders were coated onto a Kimwipe® wiper as described in Example 1. After drying, the add-on level was approximately 2%.

The samples were then tested for odor adsorption as described above using 1.96 milligrams of pyridine. The results are shown below in Table 5 in terms of milligrams of the odorous compound removed per gram of sample, i.e., relative adsorption efficiency, and percent odor removed.

TABLE 5

Removal of Pyridine

| Sample | Relative Adsorption Efficiency (mg odor removed/g sample) | % Odor removed |
|---|---|---|
| Snowtex-C | 105 | 78 |
| Snowtex-AK | 84 | 68 |

As indicated, the colloidal silica nanoparticles were capable of effectively adsorbing the pyridine odor when contained on a substrate.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A substrate for reducing odor, said substrate being porous and comprising a nonwoven, woven, or paper web, said substrate containing colloidal silica nanoparticles configured to adsorb one or more odorous compounds, said silica nanoparticles having an average size of from about 1 to about 50 nanometers and a surface area of from about 50 to about 1000 square meters per gram, wherein the silica nanoparticles are relatively nonporous and thus have a pore volume of less than about 0.4 milliliters per gram.

2. A substrate as defined in claim 1, wherein said colloidal nanoparticles have an average size of from about 4 to about 20 nanometers.

3. A substrate as defined in claim 1, wherein said colloidal nanoparticles have a surface area of from about 100 to about 600 square meters per gram.

4. A substrate as defined in claim 1, wherein said colloidal nanoparticles have a pore volume of less than about 0.3 milliliters per gram.

5. A substrate as defined in claim 1, wherein the solids add-on level of said colloidal nanoparticles is from about 0.001% to about 20%.

6. A substrate as defined in claim 1, wherein said colloidal nanoparticles cover at least about 50% of a surface of said substrate.

7. A substrate as defined in claim 1, wherein said colloidal nanoparticles cover at least about 80% of a surface of said substrate.

8. A substrate as defined in claim 1, wherein said colloidal nanoparticles are coated onto a surface of said substrate, said coating having a thickness of less than about 1 micron.

9. A substrate as defined in claim 8, wherein said coating has a thickness of from about 2 to about 500 nanometers.

10. An absorbent article that comprises the substrate of claim 1.

11. An absorbent article as defined in claim 10, further comprising at least one liquid-transmissive layer and a liquid-absorbent core, wherein said substrate forms at least a portion of said liquid-transmissive layer, said liquid-absorbent core, or combinations thereof.

12. An absorbent article as defined in claim 11, wherein the absorbent article includes a liquid-transmissive liner, a liquid-transmissive surge layer, a liquid-absorbent core, and a vapor-permeable, liquid-impermeable outer cover, said substrate forming at least a portion of said liner, said surge layer, said absorbent core, said outer cover, or combinations thereof.

13. A paper product that comprises the substrate of claim 1.

14. A facemask that comprises the substrate of claim 1.

15. A substrate as defined in claim 1, wherein said silica nanoparticles are coated with alumina.

16. A substrate as defined in claim 1, wherein said substrate has a porosity such that from about 20 to about 500 cubic feet of air is capable of flowing through 1 square foot of said substrate per minute under a pressure differential of 125 Pascals.

17. A substrate as defined in claim 1, wherein said substrate is a paper web.

18. A substrate as defined in claim 1, wherein said substrate is a nonwoven web.

19. A substrate as defined in claim 1, wherein said silica nanoparticles consist essentially of silica or alumina coated silica.

\* \* \* \* \*

UNITED STATES PATENT AND TRADEMARK OFFICE
CERTIFICATE OF CORRECTION

| | | |
|---|---|---|
| PATENT NO. | : 7,879,350 B2 | Page 1 of 1 |
| APPLICATION NO. | : 10/686933 | |
| DATED | : February 1, 2011 | |
| INVENTOR(S) | : John Gavin MacDonald et al. | |

It is certified that error appears in the above-identified patent and that said Letters Patent is hereby corrected as shown below:

Title Page item 56

Under References Cited - Foreign Patent Documents the following reference needs to be added:

EP 0232141 A1   8/1987

Signed and Sealed this
Fourth Day of October, 2011

David J. Kappos
*Director of the United States Patent and Trademark Office*